US009839541B2

(12) United States Patent
Costello (10) Patent No.: US 9,839,541 B2
(45) Date of Patent: Dec. 12, 2017

(54) RECONSTRAINABLE STENT SYSTEM (75) Inventor: Kieran Costello, Cullenagh (IE)

(73) Assignee: Cook Medical Technologies LLC, Bloomington, IN (US)

( * ) Notice: Subject to any disclaimer, the term of this patent is extended or adjusted under 35 U.S.C. 154(b) by 196 days.

(21) Appl. No.: 13/589,320

(22) Filed: Aug. 20, 2012

(65) Prior Publication Data
US 2013/0053941 A1 Feb. 28, 2013

Related U.S. Application Data (60) Provisional application No. 61/526,078, filed on Aug. 22, 2011.

(51) Int. Cl.
A61F 2/88 (2006.01)
A61F 2/95 (2013.01)
A61F 2/962 (2013.01)
A61F 2/966 (2013.01)

(52) U.S. Cl.
CPC ............ A61F 2/88 (2013.01); A61F 2/95 (2013.01); A61F 2/962 (2013.01); A61F 2002/9528 (2013.01); A61F 2002/9665 (2013.01); A61F 2230/0078 (2013.01)

(58) Field of Classification Search
CPC .... A61F 2/88; A61F 2/885; A61F 2/89; A61F 2/90; A61F 2/91; A61F 2/915; A61F 2/95; A61F 2/9528; A61F 2/9534; A61F 2/962; A61F 2230/0078; A61F 2002/9665; A61F 2002/9583; A61F 2002/9511; A61F 2002/9528; A61F 2002/9534; A61B 2017/12054; A61B 2017/12077

USPC ......... 623/1.11, 1.35, 1.12, 1.15, 1.16, 1.13, 623/1.23, 1.19–1.21; 606/194, 192, 108, 606/195, 228; 604/523
See application file for complete search history.

(56) References Cited

U.S. PATENT DOCUMENTS

| 5,695,499 | A | 12/1997 | Helgerson et al. |
| 5,830,179 | A * | 11/1998 | Mikus et al. ............... 604/517 |
| 6,716,238 | B2 | 4/2004 | Elliott |
| 6,872,433 | B2 | 3/2005 | Seward et al. |
| 7,264,631 | B2 | 9/2007 | DiCarlo |
| 7,947,070 | B2 | 5/2011 | Headley et al. |
| 2003/0040772 | A1* | 2/2003 | Hyodoh et al. ............ 606/200 |
| 2005/0197690 | A1* | 9/2005 | Molaei et al. ............. 623/1.13 |
| 2005/0256562 | A1 | 11/2005 | Clerc et al. |
| 2006/0190075 | A1* | 8/2006 | Jordan et al. ............. 623/1.23 |
| 2006/0276887 | A1 | 12/2006 | Brady et al. |
| 2007/0179529 | A1* | 8/2007 | Doyle ......................... 606/228 |

(Continued)

FOREIGN PATENT DOCUMENTS

| WO | WO 2011/094527 A1 | 8/2011 |
| WO | WO 2011/094586 A1 | 8/2011 |

OTHER PUBLICATIONS

Notification of Transmittal of the International Search Report and the Written Opinion of the International Searching Authority, or the Declaration, dated Nov. 20, 2012, for corresponding application PCT/US2012/051529, 6p.

(Continued)

Primary Examiner — Jocelin Tanner
(74) Attorney, Agent, or Firm — Brinks Gilson & Lione (57) ABSTRACT A system for the delivery and repositioning of a stent is provided that allows the stent to be reconstrained after full or partial expansion for deployment to and removal from a target region.

11 Claims, 4 Drawing Sheets (56) References Cited

U.S. PATENT DOCUMENTS

| | | |
|---|---|---|
| 2007/0270931 A1 | 11/2007 | Leanna et al. |
| 2007/0270937 A1 | 11/2007 | Leanna |
| 2008/0033528 A1* | 2/2008 | Satasiya .................. A61F 2/91 623/1.15 |
| 2008/0243225 A1 | 10/2008 | Satasiya et al. |
| 2009/0082840 A1 | 3/2009 | Rusk et al. |
| 2010/0094394 A1 | 4/2010 | Beach et al. |
| 2011/0071613 A1 | 3/2011 | Wood et al. |
| 2011/0190865 A1* | 8/2011 | McHugo .................. A61F 2/95 623/1.11 |
| 2012/0041538 A1 | 2/2012 | White et al. |

OTHER PUBLICATIONS

Office Action issued for corresponding European Patent Application No. EP 12754156.3, dated Oct. 25, 2017, 6p.

\* cited by examiner

RECONSTRAINABLE STENT SYSTEM

RELATED APPLICATION

This application claims the benefit of priority from U.S. Provisional Application No. 61/526,078, filed Aug. 22, 2011, and titled "Reconstrainable Stent System", the contents of which is incorporated herein by reference.

TECHNICAL FIELD

The present invention relates to medical devices and more specifically, stents.

BACKGROUND

Self expanding stents are useful for a variety of procedures requiring the maintenance of the patency of a bodily pathway. Such stents are generally biased to expand, such that when deployed, they assume an open position, pushing outward and into the surrounding area into which deployed. The radial expansion creates or maintains a pathway in a once occluded or weak area.

Deployment of a stent, such as a self expanding stent, through the use of a traditional sheath, is not desired due to the many shortcomings resulting from sheath deployment. For example, the sheath release delivery devices are difficult to reposition or remove and slow to operate. The stent may only be partially-deployed prior to reconstrainment of the stent by the sheath in order to still reposition or remove the stent. Once the stent is fully deployed, i.e. radially expanded, the sheath cannot reconstrain the stent to allow it to be repositioned or removed. For example, utilizing a conventional outer sheath/inner catheter delivery device may cause the physician to inadvertently use excessive force and pull back the outer sheath too far, thereby prematurely deploying the stent in an incorrect position within a bodily lumen. At this step in the procedure, repositioning of the stent becomes difficult, if not impossible, because the stent has already radially self-expanded into the bodily lumen. Additionally, retraction of the outer sheath in a controlled manner is often difficult which may lead to uneven or inadvertent jerking back of the outer sheath and improper positioning of the stent.

Moreover, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the proximal portion of the stent may elongate or foreshorten while still covered by the outer sheath or after the sheath releases the stent. Foreshortening is a property inherent in some self expanding stents. It is the property describing the characteristic of a stent that when in an expanded state it generally has a length shorter than when in a collapsed state. Foreshortening may result in a stent being deployed in the wrong position because the stent shortens during expansion, such as when after being deployed.

The positioning of the stent body in the central portion of the target region may also be difficult with a distal stent release system.

An additional drawback occurs with the sheathed stent delivery system where direct visualization of the stent is required. For example, with endoscopically placed stents, the sheath tends to prevent or obscure the location of the stent, making accurate placement of the stent more difficult. Accurate placement of the proximal portion of the stent and/or the stent body may be important in certain applications, for example to prevent stent migration or to properly open a stricture along the entire length of the stricture.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed (or collapsed) within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysteresis in the movement of the stent. The sheathed stent delivery device also requires more space within an endoscope compared to a sheathless device and also adds additional expense to the delivery system.

BRIEF SUMMARY

In a first aspect, a stent is provided having an elongated tubular body having a proximal portion, a distal portion, and a lumen extending between the proximal portion and the distal portion, wherein the elongated tubular body further has one or more wires; a suture having a first loop and a second loop, wherein the first loop is connected to the proximal portion of the stent; and wherein the second loop is configured to assume a first configuration when at a temperature below a first temperature and a second configuration when at a second temperature above the first temperature.

In a second aspect, a reconstrainable stent system is provided having an introducer having: an elongated tubular body having a proximal portion, a distal portion, a shoulder portion disposed at the proximal portion, and a pusher portion disposed on the elongated tubular body separate from and in a direction distal to the shoulder portion; a stent having: an elongated tubular stent body having a proximal portion, a distal portion, and a lumen extending between the proximal portion and the distal portion; a suture configured into a first loop and a second loop, wherein the first loop is connected to the proximal portion of the stent body; and wherein the second loop is configured to assume a first configuration when at a temperature below a first temperature and a second configuration when at a second temperature above the first temperature; wherein the second loop is disposed between the shoulder portion of the introducer and the pusher portion of the introducer In a third aspect, a method of delivering a reconstrainable stent is provided, the method including providing a reconstrainable stent having: a stent body configurable into an expanded state and a compressed state; and a grasping loop in communication with the stent body, wherein the grasping loop is configured to assume a first configuration when at a temperature below a first temperature and a second configuration when at a second temperature above the first temperature; providing an introducer; providing an outer sheath; connecting the grasping loop of the reconstrainable stent to the introducer; disposing a portion of the introducer through the stent body; and disposing the outer sheath over at least a portion of the introducer and the stent body, such that the grasping loop is covered by the outer sheath and the stent body is compressed by the outer sheath.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

DETAILED DESCRIPTION OF PRESENTLY PREFERRED EMBODIMENTS

The exemplary embodiments illustrated herein provide exemplary apparatuses for delivering, repositioning, and removing a stent. The present invention is not limited to those embodiments described herein, but rather, the disclosure includes all equivalents and those intended to be included in the claims. For example, the principles herein can be applied to other types of stents, including but not limited to, self expanding metal stents, self expanding laser cut peripheral artery stents, laser cut balloon expandable stents, laser cut self expanding stents, woven wire stents, and the EVOLUTION® (Wilson-Cook Medical Inc.).

Moreover, the embodiments illustrated herein can be used in any portion of the body benefiting from an indwelling medical device, such as a stent, that will benefit from being able to be repositioned or removed after partial or full deployment, including but not limited to, the gastrointestinal region, esophageal region, duodenum region, biliary region, colonic region, as well as any other bodily region or field, and they are not limited to the sizes, shapes, or configurations illustrated herein.

The term patient, as used herein, is not limited to being a human being; animals and others are contemplated. The term user, as used herein, is anyone or thing capable of using the device, including but not limited to, a human being and machine.

A more detailed description of the embodiments will now be given with reference to FIGS. 1-7. Throughout the disclosure, like reference numerals and letters refer to like elements. The present disclosure is not limited to the embodiments illustrated; to the contrary, the present disclosure specifically contemplates other embodiments not illustrated but intended to be included in the claims.

It has been discovered that the delivery, repositioning, and removing of a stent, such as a self expanding metal stent, including but not limited to an esophageal stent, can be improved through a system that permits the stent to be expanded or partially expanded for deployment and later reconstrained for repositioning or removal.

Figure 1:
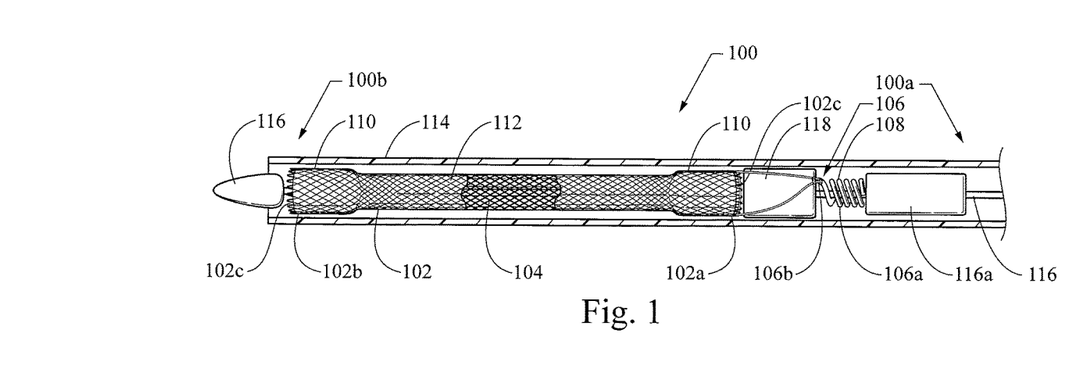
FIG. 1 illustrates a side view of an exemplary reconstrainable stent system wherein an exemplary stent is covered by an outer sheath.
Figure 2:
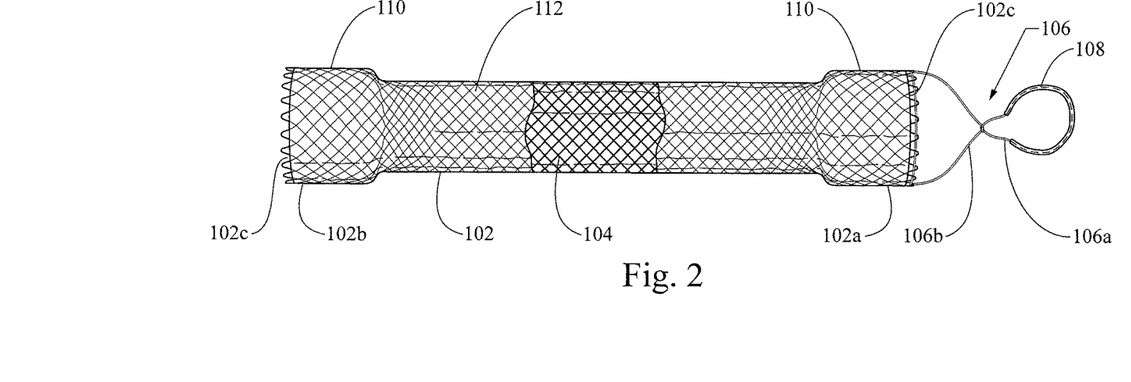
FIG. 2 illustrates a side view of an exemplary stent for use in the exemplary system illustrated in FIG. 1.

FIG. 1 illustrates a side view of exemplary reconstrainable stent system 100 wherein exemplary stent 102 is covered by outer sheath 114. FIG. 2 illustrates a side view of exemplary stent 102 for use in exemplary system 100 illustrated in FIG. 1. Referring to FIGS. 1-2, stent 102 is preferably a self-expanding metal stent, although other stents are contemplated. Stent 102 includes an elongated generally tubular body having proximal portion 102a, distal portion 102b, and lumen 102c extending therebetween. Stent 102 comprises one or more wires 104, preferably comprising a woven-helical pitch. Stent 102 is configured to assume an expanded state having a diameter greater than a collapsed or partially-collapsed state, and it is generally configured for holding open or repairing a bodily pathway, such as a diseased or damaged bodily lumen.

As will be described in greater detail below, expandable stents illustrated and equivalents thereto may be formed from a variety of biocompatible materials. Wires 104 preferably comprise one or more elastically deformable materials such as shape memory alloys (e.g., stainless steel, nitinol, and the like), although other materials are contemplated. Wires 104 may also be made from or comprise any suitable biocompatible material(s). For example, stents illustrated and equivalents thereto may include materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

Stents illustrated and equivalents thereto may be fabricated to any suitable dimensions. Stents illustrated and equivalents thereto having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter.

A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

Stents illustrated and equivalents thereto may include a central body portion and one or more uniform flanges, or it may have two asymmetrically shaped flanges. A stent may include a uniform diameter along the length of stent but include slightly flared 110 proximal end 102a and/or distal end 102b of the stent 102. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the proximal and distal ends engage healthy tissue adjacent the diseased area. Although stent 102 is depicted as having a substantially uniform diameter on the longitudinal axis and flares 110 having a slightly larger diameter than the body portion, other stent configurations are possible.

Stents illustrated and equivalents thereto may have any suitable helical pattern or angle such as those illustrated in FIGS. 1-3 and 5-7, as further discussed below. The radial force of the stent may be controlled by adjusting the angle accordingly. Stents with higher angles typically exert greater radial force and exhibit greater foreshortening during expansion from a compressed state. Stents with lower angles typically exert lower radial force and experience less foreshortening upon expansion. In some instances, the angle can be lowered because the membrane covering typically adds rigidity to the stent structure. In addition to adjusting the angle, the radial force of the stent can be adjusted through selection of particular filament materials, as well as the shape and size of the filaments or wires forming the stent structure.

Stents illustrated and equivalents thereto may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of wires 104. In some embodiments, a stent may include four radiopaque markers with two markers affixed to a first flange and two to a second flange. Optionally, radiopacity can be added to a stent through covering (also referred to as coating) processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

Stents illustrated and equivalents thereto may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents may be preferred for use in vessels that are subject to changes in shape and/or changes in position, such as those of the peripheral and gastrointestinal systems. Peripheral vessels regularly change shape as the vessels experience trauma from external sources (e.g., impacts to arms, legs, etc.); and many gastrointestinal vessels naturally change shape as peristaltic motion advances food through the digestive tract.

Mechanically expandable stents (e.g., balloon expandable stents) may be made from plastically deformable materials (e.g., 316L stainless steel). A balloon-expandable stent may be crimped and delivered in a reduced diameter and thereafter expanded to a precise expanded diameter. Balloon expandable stents can be used to treat stenosed coronary arteries, among other vessels. One common procedure for implanting a balloon expandable stent involves mounting the stent circumferentially on a balloon-tipped catheter and threading the catheter through a vessel passageway to the target area. Once the balloon is positioned at the targeted area, the balloon may be inflated to dilate the vessel and radially expand the stent. The balloon may then be deflated and removed from the passageway.

Although covering 112 of stent 102 is illustrated as being a silicone elastomer, which is desired given its ability to stretch generally 500-700% without being compromised and such, is useful in stent applications, other covering materials are contemplated, including but not limited to, polyethylene (the fibers of which could be applied in layers at the same pitch of wires 104 to help close the gaps and provide a seal-like covering (but an air or water-tight seal need not be achieved)), TYVEK® (DuPont) (or other like materials) which are contemplated as being disposed between wires 104, as well as other materials, including but not limited to, non-woven materials. Indeed it is also completed that other fabric layers with filaments running in one direction that matches the pitch of one or more of stent wires 104 could be used as a covering. As such, the covering could be made up of several layers with the filaments running in one direction with a pitch similar to one or more of wires 104 with the direction of the helical pattern alternated between layers. It is contemplated that such fabric layer may be bonded to one or more of wires 104.

Indeed, in some embodiments, the covering membrane may cover over the entire stent framework from the proximal end 102a to the distal end 102b. In other embodiments, the stent may have a covering over a central portion of the structure and one or more uncovered ends or flanges. Moreover, a membrane covering may comprise any suitable biocompatible material. Preferably, the membrane covering is an elastic or flexible material that can adapt to radial compression of a stent prior to delivery, as well as foreshortening of a stent during expansion from a compressed state. Suitable membrane materials include, for example, as discussed above, silicones (e.g. polysiloxanes and substituted polysiloxanes), polyurethanes, thermoplastic elastomers, polyolefin elastomers, polyethylene, polytetrafluoroethylene, nylon, and combinations thereof. In some embodiments, where the stent will be implanted at or near an acidic environment (e.g., being exposed to gastric fluids), preferably the membrane covering is resistant to acid degradation.

Stents illustrated and equivalents thereto may include a membrane covering applied by any suitable method as is known in the art. For example, the membrane may be applied by spraying, dipping, painting, brushing, or padding. Generally, the membrane covering has a thickness ranging from about 0.0025 mm to about 2.5 mm, from about 0.01 mm to about 0.5 mm, or from about 0.03 mm to about 0.07 mm. The thickness of the membrane may be selected, for example, by controlling the number of dips or passes made during the application process.

In some embodiments, a stent may include one or more bioactive agents coated on the stent surfaces. A bioactive agent may be applied directly on the surface of the stent (or on a primer layer which is placed directly on the surface of the stent). Alternatively, the bioactive agent may be mixed with a carrier material and this mixture applied to the stent.

In such configuration, the release of the bioactive agent may be dependent on factors including composition, structure, and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the stent and then over coated with barrier layer(s). Multiple layers of bioactive agent, or mixtures of carrier material/bioactive, separated by barrier layers may be present to form a stent having multiple coverings. Different bioactive agents may be present in the different layers.

The carrier material and/or the barrier layer can include a bioelastomer, PLGA, PLA, PEG, Zein, or a hydrogel. In some other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. The carrier material and/or barrier layer may include lactose, dextrose, mannitol, a derivative of lactose, dextrose, mannitol, starch, or a starch derivative. The carrier material and/or barrier layer may include a biostable or a biodegradable material, for example, a biostable, or biodegradable polymer.

A variety of bioactive agents may be applied to the stent in accordance with the intended use. For example, bioactive agents that may be applied include antiproliferative/antimitotic agents including natural products such as vinca alkaloids (vinblastine, vincristine, and vinorelbine), paclitaxel, rapamycin analogs, epidipodophyllotoxins (etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) II b/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat.

A bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition, or any other method known.

Prior to applying a membrane covering, and/or a bioactive agent, a stent may be polished, cleaned, and/or primed as is known in the art. A stent may be polished, for example, with an abrasive or by electropolishing. A stent may be cleaned by inserting the stent into various solvents, degreasers, and cleansers to remove any debris, residues, or unwanted materials from the stent surfaces. Optionally, a primer coating may be applied to the stent prior to application of a membrane covering, bioactive, or other coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure. A primer layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

Still referring to FIGS. 1-2, stent 102 includes suture 106. Suture 106 is a thread-like member that may comprise any appropriate biocompatible material, such as for example, suture materials or other polymeric or metallic materials such as polyethylene, ultra-high molecular weight polyethylene, polyester, nylon, stainless steel, nitinol, or the like. Optionally, suture 106 may be covered with a material including but not limited to, polytetrafluoroethylene (PTFE), to reduce frictional interactions of the suture with surrounding tissue or to prevent accidently severing of suture 106.

Suture is knotted into two places to create two loops 106a, 106b. Suture 106 is positioned and sized so that it does not interfere with the flow of material, such as food, bile, or blood, through lumen 102c of stent 102. Moreover, the ability of stent 102 to fully or partially collapse and expand is not impaired by suture 106.

First loop 106b is threaded into proximal portion 102a of stent 102 such that it is connected to stent 102. Other means for connecting first loop 106b to stent 102 are contemplated. Other connection locations are contemplated.

The second loop forms grasping loop 106a and is preferably passed through suture covering 108. Suture covering 108 is preferably a tube made from nitinol, although other configurations and materials are contemplated, including other shape memory alloys and those having properties similar to nitinol such that the material can be shape-biased to assume a first shape when deformed into a second shape when exposed to certain elements, such as temperature or a range of temperatures. Other configurations are contemplated, including but not limited to, forming suture 106 in whole or in part from suitable suture covering materials rather than having suture covering configured as a separate component disposed about grasping loop 106a.

Grasping loop 106a is preferably disposed proximal to proximal portion 102a of stent 102. However, other configurations are contemplated, including but not limited to, disposing grasping loop 106a or any portion thereof inside lumen 102c of stent 102 or next to stent 102.

As is illustrated in FIG. 2, suture covering 108 is heat-set to perform a shape-memory function such that it is biased to assume a loop shape when at body temperature (at or near about 37° C. depending upon the location of the stent and the condition of the patient or any other desired temperature). When at room temperature (or a temperature below that which it was heat-set to activate), suture covering 108 may be mechanically deformed into any number of shapes. Thus, grasping loop 106a is configured to assume a first configuration when at a temperature below a first temperature and a second configuration when at a temperature above the first temperature.

Alternatively, any one of first loop 106b or grasping loop 106a, including a first configuration for grasping loop 106a or and second configuration for grasping loop 106a, can be configured into any other shape, including but not limited to, a square, rectangle, and triangle. Accordingly, the term loop as used herein is not defined as requiring a circular or near-circular shape. Rather, the term is used to describe a perimeter for any number of shapes into which suture 106 or portions thereof can be configured.

Suture 106 facilitates the delivery, repositioning, and removal of stent 102 during implantation. More specifically, grasping loop 106 allows stent 102 to be connected to introducer 116 (a pushing catheter). Introducer 116 includes pusher 118 and shoulder 116a disposed about the outer surface of introducer 116 which secure grasping loop 106a therebetween to introducer 116.

Figure 3:
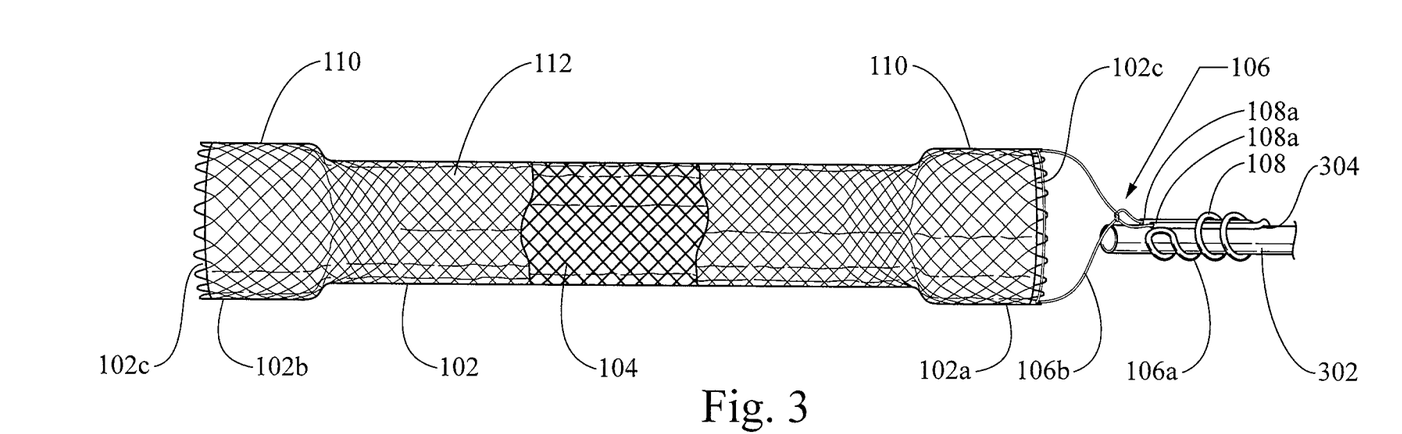
FIG. 3 illustrates an exemplary suture of the exemplary stent illustrated in FIG. 2 being formed for use with an introducer.
Figure 4:
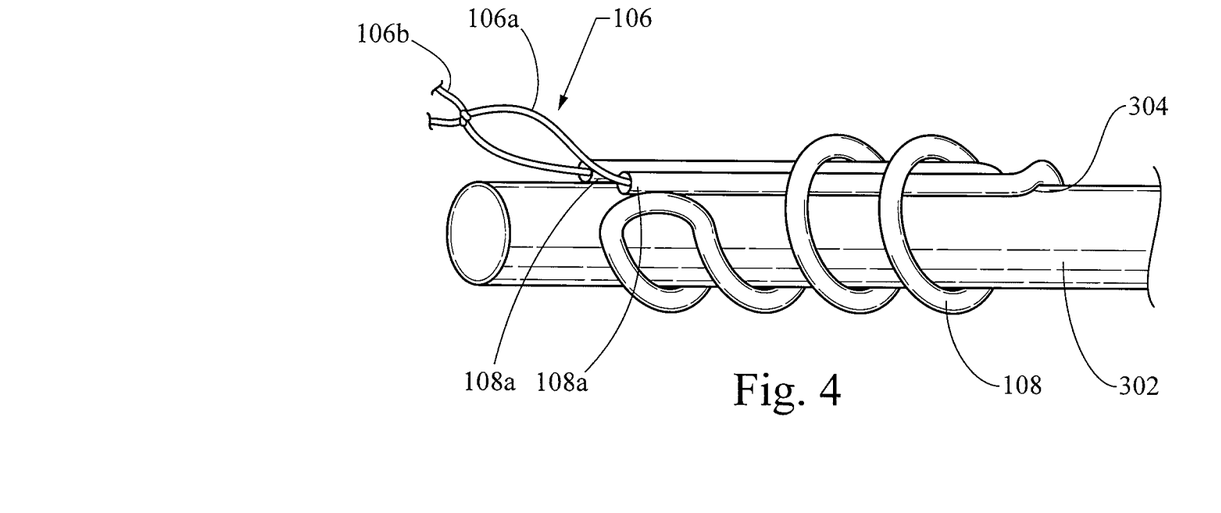
FIG. 4 is a close up perspective view of that which is illustrated in FIG. 3.

FIG. 3 illustrates exemplary suture 106 of exemplary stent 100 illustrated in FIG. 2 being formed for use with introducer 116, illustrated in FIG. 1. FIG. 4 is a close up perspective view of that which is illustrated in FIG. 3. Referring to FIGS. 3-4, grasping loop 106a having suture covering 108 is wrapped around a generally cylindrical mandrel 302 to create suture lumen 304 having a diameter about the size of the outer diameter of mandrel 302. Preferably, suture lumen 304 should be sized about the same size as the outer diameter of introducer 116. Numerous wrapping configurations are contemplated to form suture lumen 304. As can best be seen in FIG. 4, one exemplary method for forming suture lumen 304, includes but is not limited to, first placing ends of suture covering 108a onto mandrel 302 such that ends of suture covering 108a are longitudinally oriented to a portion of mandrel 302. Second, the remaining looped suture covering is then wrapped over ends of suture covering 108a forming suture lumen 304. Mandrel 302 is removed from suture lumen 304.

Alternatively, a suture lumen can be configured by wrapping grasping loop 106a or portion thereof, around introducer 116 or any other suitably-sized object.

Stents illustrated and equivalents thereto may be delivered to a bodily lumen using various techniques, including by use of the devices and methods illustrated in FIGS. 1, 5-7 and equivalents thereof.

Figure 5:
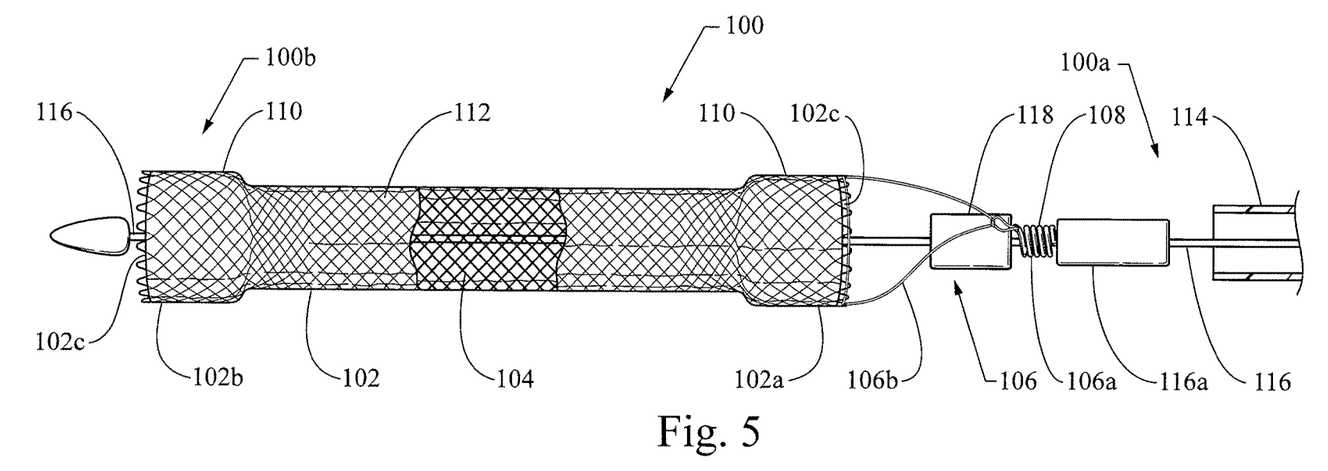
FIG. 5 illustrates the exemplary stent illustrated in FIG. 2 attached to an introducer.

FIG. 5 illustrates exemplary stent 102 illustrated in FIG. 2 attached to introducer 116. Stent 102 is loaded onto introducer 116, preferably such that shoulder 116a of introducer 116 is in a direction proximal to that of suture 106 and introducer 116 is coaxial with lumen 102c of stent 102 and suture lumen 304. Other configurations are contemplated.

Pusher 118 is attached to introducer 116 such that pusher 118 is preferably coaxial with introducer 116, is separate from shoulder 116a, and secures wrapped grasping loop 106a between shoulder 116a of introducer 116 and pusher 118. Other configurations are contemplated. Pusher 118 can be attached by numerous attachment means, including but not limited to, glue, soldering, and a threaded attachment mechanism. Stent 102 is now secured to introducer 116.

Referring now to FIGS. 1 and 5, outer sheath 114 is directed over introducer 116 and stent 102 such that outer sheath 114 is preferably coaxial with introducer 116 and sheath 102. Other configurations are contemplated. Outer sheath 114 compresses stent 102 from its expanded state (illustrated in FIG. 5) to a collapsed state (illustrated in FIG. 1) such that the diameter of stent 102 is reduced when in a collapsed state as compared to an expanded or partially expanded state.

Any one of or all of pusher 118, introducer 116, shoulder 116a, suture covering 108, and outer sheath 114 may include one or more components configured to aid in visualization and/or adjustment of stent 102 during implantation, repositioning, or retrieval. For example, any one of or all of pusher 118, introducer 116, shoulder 116a, suture covering 108, and outer sheath 114 may include one or more radiopaque markers configured to provide for fluoroscopic visualization for accurate deployment and positioning. Radiopaque markers may be affixed (e.g., by welding, gluing, suturing, or the like) at or near the ends of any one of or all of pusher 118, introducer 116, shoulder 116a, suture covering 108, and outer sheath 114. Optionally, radiopacity can be added through covering (also referred to as coating) processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

System 100 is directed to the targeted bodily location under any reasonable means, including but not limited to, fluoroscopy and direct endoscopic visualization, such that distal portion 100b is directed closest to the targeted location, and proximal portion 100a extends towards the user of system 100. The targeted lumen may be predilated with a balloon catheter or other dilation device, if necessary or desired.

Figure 6:
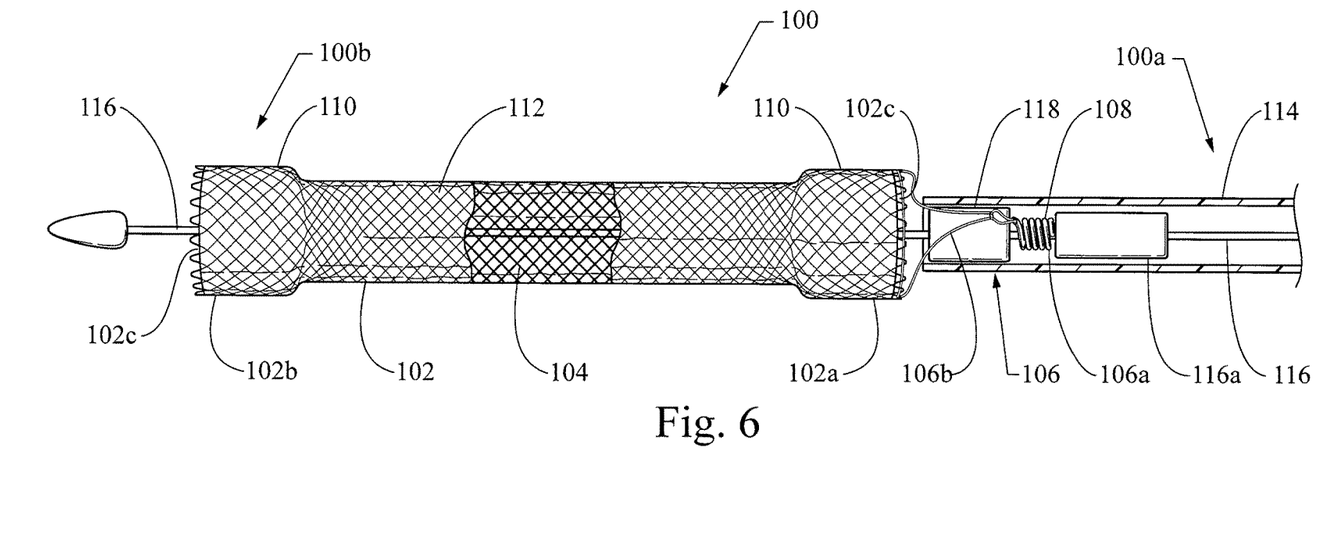
FIG. 6 illustrates the outer sheath exposing the exemplary stent wherein the stent is expanded.

FIG. 6 illustrates outer sheath 114 exposing exemplary stent 102 wherein stent 102 is in an expanded state such that its diameter is greater than when in a collapsed state. As is illustrated in FIG. 6, stent 102 can be reconstrained by pushing outer sheath 114 over stent 102. Stent 102 continues to be reconstrainable as long as outer sheath 114 does not expose grasping loop 106*a* to the activating element for grasping loop 106*a* to resume its shaped-biased state, such as a temperature or range of temperatures or removal of a constraint (e.g. outer sheath 114). Stent 102 is held in place by grasping loop 106*a* wrapped around introducer 116 which will maintain its wrapped lumen configuration until subjected to bodily temperature (or whatever temperature at which it was heat-set to activate) wherein it will revert to its shape-biased state (illustrated in FIG. 2). Alternatively, stent 102 can be partially-collapsed or partially-expanded into any number of positions by only partially advancing or retracting outer sheath 114. Accordingly, stent 102 may be repositioned without damaging the surrounding tissue or bodily structures because it is able to be reconstrained after expansion or partial-expansion.

Figure 7:
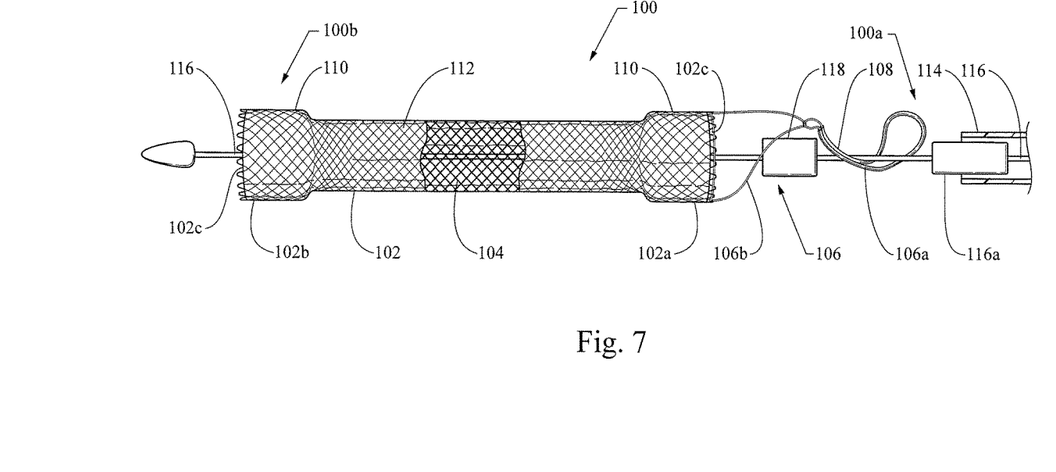
FIG. 7 illustrates the outer sheath exposing the exemplary grasping loop of the exemplary stent wherein the grasping loop has expanded.

FIG. 7 illustrates outer sheath 114 exposing exemplary grasping loop 106*a* of exemplary stent 102 wherein grasping loop 106*a* has begun to expand, resume, and recover its shape-biased state (illustrated in FIG. 2) after having been activated by body temperature (or whatever temperature at which it was heat-set to activate). Grasping loop 106*a* will unravel from introducer 116 and detach therefrom permitting introducer 116 to be retracted from stent 102 and grasping loop 106*a*.

Referring again to FIG. 2, after activation, grasping loop 106*a* will resume its shape-biased state. Grasping loop 106*a* then provides an additional means for retrieving stent 102 when no longer desired or needed to be indwelling within a patient. For example, a medical grasper having jaws, teeth, or a hook at its distal portion may be introduced into the patient by numerous means, including but not limited to, a working channel of an endoscope, and it may be directed and attached to grasping loop 106 to retrieve stent 102 from the patient.

It is contemplated that the grasping loop could be configured such that it has a super-elastic nitinol wire disposed within a PTFE sleeve having a suture loop. The wire, for example, may be heat-set to form a loop shaped grasping wire. The wire would then be wrapped around the introducer as illustrated.

It is contemplated that stent 102 could be supplied in a pre-loaded or non-preloaded orientation with respect to introducer 116. A non-preloaded orientation is possible because grasping loop 106*a* can later be loaded onto introducer 116 by collapsing stent 102 onto introducer 106*a* if grasping loop 106*a* is attached to introducer 116.

Additionally, it is contemplated that introducer 116 could be designed such to include a mechanical or visual stop indicating to the user that stent 102 is about to be automatically released from introducer 116. This could allow stent 102 to be deployed fully from introducer 116 but still be recapturable. A subsequent action would then be needed from the user to fully release stent 102 from introducer 116.

Numerous advantages of the system are evident, including but not limited to, the ability to deploy and recapture a stent for repositioning and removal. An additional advantage, includes but is not limited to, that the system negates the need for using stent lock wires, which generally are needed in stent-recapturable systems. Typically, a stent lock wire would extend through an introducer from the stent to the handle, thereby locking the stent to the introducer. Pulling the stent lock wire would release the stent from the introducer. Stent lock wires are not desired because the actions necessary to remove the stent lock wire from the introducer can be forgotten by the user, thereby resulting in the stent being inadvertently pulled out with the introducer.

From the foregoing, the discovery of a system for the delivery and repositioning of a stent benefits a patient by reducing trauma to the surrounding tissue and by more accurate and efficient stent placement and removal.

It can be seen that the systems, apparatuses, and methods illustrated and equivalents thereof may utilize machines or other resources, such as human beings, thereby reducing the time, labor, and resources required to manufacturer or use a stent and a delivery device. Indeed, the discovery is not limited to the embodiments illustrated herein, and the principles and methods illustrated herein can be applied and configured to any stent, delivery system, and equivalents.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of the discovery. Furthermore, the advantages described above are not necessarily the only advantages, and it is not necessarily expected that all of the described advantages will be achieved with every embodiment.

What is claimed is:

1. A stent system comprising:
an elongated tubular body comprising a proximal portion, a distal portion, and a lumen extending between the proximal portion and the distal portion, wherein the elongated tubular body further comprises one or more wires;
a suture comprising a grasping loop, wherein the grasping loop is connected to the proximal portion of the stent;
wherein the grasping loop is configured to assume a first configuration when at a temperature below a first temperature and a second configuration when at a second temperature above the first temperature, the grasping loop being adapted to be at least partially circumferentially disposed about and removably secured to an elongate tubular introducer member when in the first configuration, and adapted to be laterally separable from the tubular introducer member when in the second configuration,
wherein the grasping loop forms a helical coil shape when in the first configuration, the helical coil shape defining a lumen adapted to receive the elongate tubular introducer member there through,
wherein the grasping loop forms a non-helical coil shape when in the second configuration, and
wherein the stent is circumferentially disposed about an elongate tubular introducer member, wherein the grasping loop is helically disposed about and coupled to the elongate tubular introducer member when in the first configuration, and wherein the grasping loop is uncoupled from the elongate tubular introducer member when in the second configuration.

2. The stent of claim 1, wherein the first temperature is about 37° C.

3. The stent of claim 1, wherein the grasping loop further comprises a nitinol structure, the nitinol structure configured to assume the first configuration when at the temperature below the first temperature, and the second configuration when at the second temperature above the first temperature.

4. The stent of claim 1, wherein the grasping loop further comprises a suture covering disposed about an outer surface of the grasping loop.

5. The stent of claim 4, wherein the suture covering comprises a nitinol tube wherein at least a portion of the grasping loop is disposed through the nitinol tube.

6. The stent of claim 1 further comprising a covering affixed to the one or more wires of the elongate tubular body.

7. The stent of claim 1, wherein the one or more wires comprise nitinol.

8. The stent of claim 1, wherein the one or more wires are woven and helically wound.

9. The stent of claim 1, wherein the stent is a self-expanding metal stent.

10. The stent of claim 1, wherein the grasping loop forms a planar shape when in the second configuration.

11. The stent of claim 1, wherein the grasping loop comprises a suture portion woven about a proximal end of the stent.

* * * * *